(12) United States Patent
Gallenkamp et al.

(10) Patent No.: US 7,585,998 B2
(45) Date of Patent: Sep. 8, 2009

(54) METHOD FOR PRODUCING DIFLUORO-ACETYL-ACETIC ACID ALKYLESTERS

(75) Inventors: Bernd Gallenkamp, Wuppertal (DE); Lubbertus Mulder, Hagen (DE)

(73) Assignee: Bayer CropScience AG, Monheim (DE)

( * ) Notice: Subject to any disclaimer, the term of this patent is extended or adjusted under 35 U.S.C. 154(b) by 593 days.

(21) Appl. No.: 10/561,031

(22) PCT Filed: Jun. 18, 2004

(86) PCT No.: PCT/EP2004/006607

§ 371 (c)(1),
(2), (4) Date: Dec. 16, 2005

(87) PCT Pub. No.: WO2005/003077

PCT Pub. Date: Jan. 13, 2005

(65) Prior Publication Data

US 2006/0149091 A1    Jul. 6, 2006

(30) Foreign Application Priority Data

Jul. 1, 2003  (DE) ............................... 103 29 450
Jul. 11, 2003 (DE) ............................... 103 31 496

(51) Int. Cl.
C07C 69/66 (2006.01)
(52) U.S. Cl. .................................... 560/174
(58) Field of Classification Search ................ 560/155, 560/174; 558/179
See application file for complete search history.

(56) References Cited

U.S. PATENT DOCUMENTS

| | | | |
|---|---|---|---|
| 4,484,993 A | 11/1984 | Ishikawa et al. | ...... 204/158 HA |
| 2004/0039043 A1 | 2/2004 | Elbe et al. | .................... 514/406 |

FOREIGN PATENT DOCUMENTS

CA        2 476 462        8/2003

OTHER PUBLICATIONS

Tetrahedron 57, (month unavailable) 2001, pp. 2689-2700, Colin M. Tice et al, "Regiocontrolled synthesis of 3-substituted-6-trifluoromethyl-4(3H)-pyrimidinones".
Tetrahedron, vol. 52, No. 1, (month unavailable) 1996, pp. 119-130, Julia M. Dolence et al, "Synthesis of Analogs of Farnesyl Diphosphate".
Tetrahedron Letters 42 (month unavailable) 2001, pp. 4811-4814, William R. Dolbier et al, "Single electron transfer approaches to the practical synthesis of aromatic and heterocyclic-CF$_2$H derivatives".
Journal of Fluorine Chemistry, 56 (month unavailable) 1992, pp. 271-284, Tomoya Kitazume et al, "A microbially-based approach for the synthesis of chiral secondary alcohols bearing the difluoromethyl or chlorodifluoromethyl group".
Huaxue Xuebao 41(8), (month unavailable) 1983, pp. 723-729 (see p. 729), Huang Wei-yuan et al, "Study on Synthesis of Fluorochloroalky β-Diketones".
Chemical Abstracts 1984, 100, Abstract No. 22308.
Patent Abstracts of Japan Bd. 0134, Nr. 27 (C-639), Sep. 22, 1989 & JP 1 163143 A (Kashima Sekiyu KK), Jun. 27, 1989 Zusammenfassung.

Primary Examiner—Taylor Victor Oh
(74) Attorney, Agent, or Firm—Richard E. L. Henderson

(57) ABSTRACT

The present invention relates to a three-step method for the preparation of alkyl esters of 4,4-difluoroacetoacetic acid in which in the first step alkyl esters of 4-chloro-4,4-difluoroacetic acid are reacted with trialkylphosphites of formula (III)

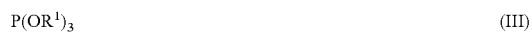

in which $R^1$ stands for $C_1$-$C_4$-alkyl, whereby the residues $R^1$ can in each case be the same or different, to form alkyl phosphonates of formula (IV)

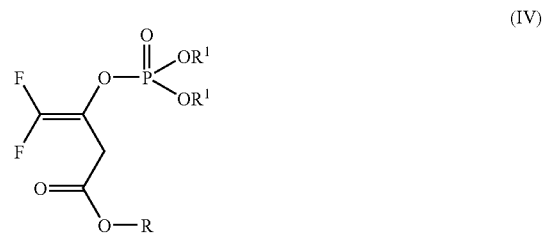

which in the next step are reacted with an amine of formula (V),

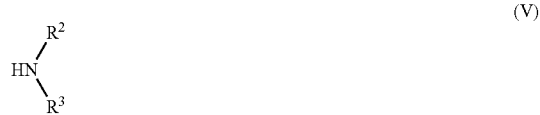

in which $R^2$ and $R^3$ independent of each other stand for hydrogen or $C_1$-$C_4$-alkyl or together form —CH$_2$—CH$_2$—O—CH$_2$—CH$_2$—,
to form enamines of formula (VI),

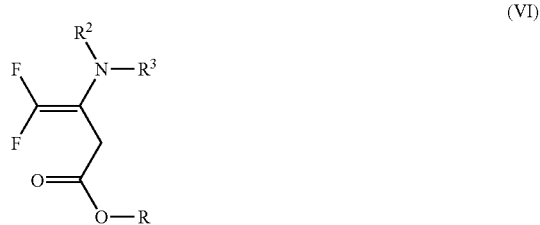

in which $R^2$ and $R^3$ have the meanings described above, which in the third step are hydrolyzed in the presence of an acid.

9 Claims, No Drawings

METHOD FOR PRODUCING DIFLUORO-ACETYL-ACETIC ACID ALKYLESTERS

The present patent application has been filed under 35 U.S.C. 371 as a national stage application of PCT/EP2004/006607, filed Jun. 18, 2004, which was published in German as International Patent Publication WO 2005/003077 on Jan. 13, 2005, and is entitled to the right of priority of German Patent Applications 10329450.3, filed Jul. 1, 2003, and 10331496.2, filed Jul. 11, 2003.

The present invention relates to a new method for the preparation of alkyl esters of 4,4-difluoroacetoacetic acid (alkyl esters of 4,4-difluoro-3-oxobutanoic acid) from alkyl esters of 4-chloro-4,4-difluoroacetoacetic acid that are in turn obtained from alkyl esters of 2-chlorodifluoroacetic acid.

It is already known that ethyl 4,4-difluoroacetoacetate can be obtained by the reaction of ethyl difluoroacetate with ethyl acetate in the presence of sodium hydride (cf. *Tetrahedron* 2001, 57, 2689-2700). However, the yield from this reaction of 25% is very unsatisfactory. In addition ethyl acetoacetate obtained as byproduct is difficult to separate from the desired product.

It is also known that ethyl 4,4-difluoroacetoacetic acid can be prepared by the reaction of ethyl difluoroacetic acid with ethyl bromoacetate in the presence of zinc (cf. *Tetrahedron* 1996, 52, 119-130). However the yields of this reaction also leave much to be desired.

Moreover, a common disadvantage of both of the cited methods is that ethyl difluoroacetate used is very expensive and is thus unattractive as educt for large scale industrial production.

It is also known that a chlorodifluoroacetyl group as substituent of an aromatic can be reduced with sodium-formaldehyde sulphoxylate dihydrate (cf. *Tetrahedron Lett.* 2001, 42, 4811-4814). However, this reaction cannot be transferred to ethyl 4-chloro-4,4-difluoroacetoacetate.

The task of the present invention is thus to make available a new, economic method with which alkyl esters of 4,4-difluoroacetoacetic acid can be obtained in a high overall yield and in high purity.

Thus the subject matter of the present invention is a method for the preparation of alkyl esters of 4,4-difluoroacetoacetic acid of structure (I)

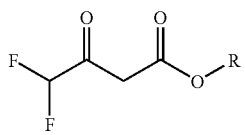

(I)

in which R stands for alkyl,
characterised in that
a) in a first step alkyl esters of 4-chloro-4,4-difluoroacetoacetic acid of structure (II)

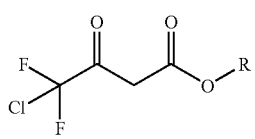

(II)

in which R has the meaning described above are reacted with trialkylphosphites of the structure (III)

$$P(OR^1)_3 \quad (III)$$

in which
$R^1$ stands for $C_1$-$C_4$-alkyl, whereby the residues $R^1$ can in each case be the same or different,
the alkyl phosphonates of structure (IV) thus obtained

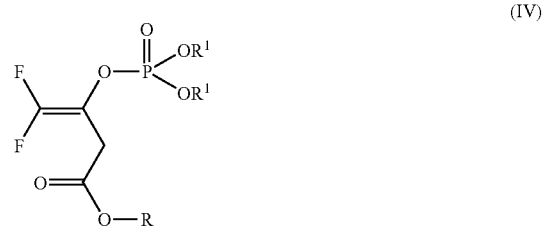

(IV)

in which R and $R^1$ have the meanings described above are reacted in a second step with an amine of structure (V)

(V)

in which
$R^2$ and $R^3$ independently of each other stand for hydrogen or $C_1$-$C_8$-alkyl or together for —$CH_2$—$CH_2$—O—$CH_2$—$CH_2$—, —$CH_2$—$CH_2$—S—$CH_2$—$CH_2$— or —$CH_2$—$CH_2$—N($R^4$)—$CH_2$—$CH_2$—,
$R^4$ stands for hydrogen or $C_1$-$C_8$-alkyl,
optionally in the presence of a diluent,
and the enamines of structure (VI) thus obtained

(VI)

in which R, $R^2$ and $R^3$ have the meanings described above is hydrolysed in a third step in the presence of an acid.

Surprisingly the alkylphosphonates of structure (IV) cannot be transformed directly into the desired final product by acid hydrolysis, rather decomposition is observed under these conditions. Equally surprising is that in the second step of the method of the invention the desired alkyl 4,4-difluoroacetoacetate and the corresponding phosphonamide are not obtained from the alkyl phosphonate of structure (IV) and an amine of structure (V), but the enamine of structure (VI) and the ammonium salt of the phosphoric acid diester. This enamine is surprisingly readily transformed into the 4,4-difluoro-acetoacetate of structure (I) by acid hydrolysis. For this isolation of the enamine is not at all necessary.

The method of the invention thus overcomes the disadvantages of known preparation procedures described above and gives alkyl esters of 4,4-difluoroacetoacetic acid in high yield and high purity. In addition the method has the advantage that esters of acetoacetic acid which can be present as impurity in alkyl esters of 4-chloro-4-difluoroacetoacetate of structure (II) can be readily removed from the reaction mixture. During the conversion esters of acetoacetic acid do not react with trialkylphosphites of structure (III) and can be removed from the alkyl phosphonates of structure (IV) by distillation.

Starting from ethyl 4-chloro-4,4-difluoroacetoacetate, trimethyl phosphite and diisoproplylamine the method of the invention can be illustrated by the following reaction scheme.

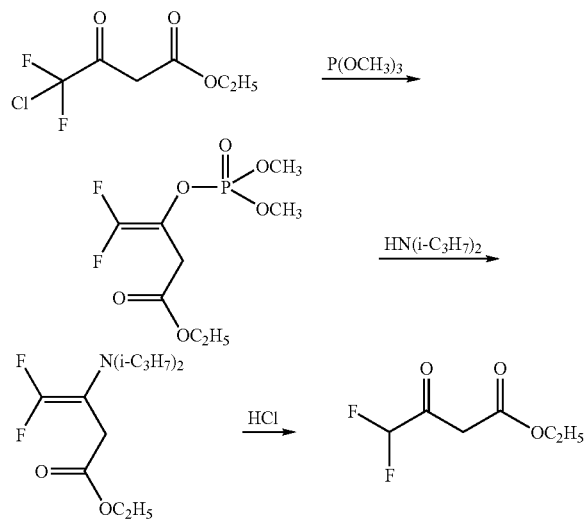

The alkyl 4,4-difluoroacetoacetates obtainable by the method of the invention can also exist in the enol form as well as the keto form shown in structure (I):

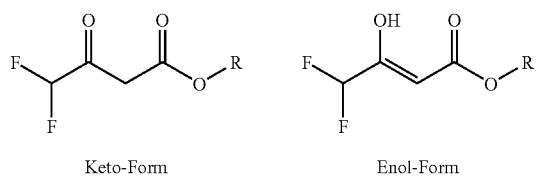

Keto-Form          Enol-Form

In addition to the alkyl 4,4-difluoroacetoacetates the hydrates of the compounds are also obtained by the method of the invention:

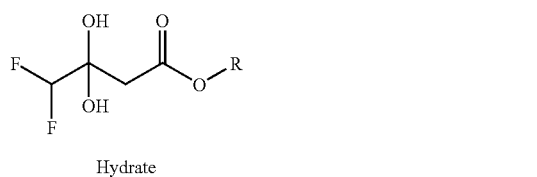

Hydrate

Thus the respective hydrate is also understood to be product of the method of the invention as well as the alkyl 4,4-difluoroacetoacetates (in keto and enol form). Depending upon the subsequent chemistry either all three forms of the product can be reacted further or respectively only certain forms (cf. below).

The alkyl 4-chloro-4,4-difluoroacetoacetates of structure (II) used as starting material in the first step (a) of the invention are known (cf. Journal of Fluorine Chemistry 1992, 56, 271-284; Huaxue Xuebao 1983, 41, 729-729 and Chemical Abstracts 1984, 100, Abstract No. 22308; EP-A 0 082 252). The may be prepared, for example, in that b) alkyl chlorodifluoroacetates of structure (VII)

(VII)

in which R has the meaning described above is reacted with alkyl acetates of structure (VIII)

(VIII)

in which R has the meaning described above in the presence of a base and in the presence of a diluent.

The alkyl phosphonates of structure (IV) and the enamines of structure (VI) are new. They may be prepared according to method (a) of the invention.

Trialkylphosphites of structure (III), amines of structure (V), alkyl chlorodifluoroacetates of structure (VII) (for possible preparation see preparation examples) and the alkyl acetates of structure (VIII) are known synthetic chemicals.

In the first step of the method (a) of the invention alkyl 4-chloro-4,4-difluoroacetoacetates of structure (II) are used in which R preferably stands for $C_1$-$C_8$-alkyl, more preferably for $C_1$-$C_6$-alkyl, most preferably for methyl, ethyl, n-, iso-propyl, n-, iso-, sec-, tert-butyl, and most particularly preferably for methyl or ethyl.

In the first step of the method (a) of the invention trialkylphosphites of structure (III) are used, in which $R^1$ can be in each case the same or different. $R^1$ stands preferably for methyl, ethyl, n-, iso-propyl, n-, iso-, sec-, tert-butyl, more preferably for methyl or ethyl.

Preferred alkyl phosphonates are such compounds of structure (IV), in which R has meanings given above as respectively preferred, more preferred, most preferred and most particularly preferred, and in which $R^1$ can be in each case the same or different and has the meaning given above as preferred or more preferred.

In the second step of the method (a) of the invention amines of structure (V) are used in which $R^2$ and $R^3$ independently of each other stand preferably for hydrogen, $C_1$-$C_6$-alkyl or together for —$CH_2$—$CH_2$—O—$CH_2$—$CH_2$—, —$CH_2$—$CH_2$—S—$CH_2$—$CH_2$— or —$CH_2$—$CH_2$—N($R^4$)—$CH_2$—$CH_2$—, more preferably for hydrogen, methyl, ethyl, n-, iso-propyl, n-, iso-, sec-, tert-butyl or together for —$CH_2$—$CH_2$—O—$CH_2$—$CH_2$—, most preferably independently of each other for iso-propyl, iso-, sec-, tert-butyl or together for —$CH_2$—$CH_2$—O—$CH_2$—$CH_2$—, most particularly preferably in each case for iso-propyl. In Structure (V) $R^4$ stands preferably for hydrogen or $C_1$-$C_6$-alkyl, more preferably for hydrogen, methyl, ethyl, n-, iso-propyl, n-, iso-, sec- or tert-butyl.

Preferred enamines are such compounds of structure (VI) in which R has the meanings given above as respectively preferred, more preferred, most preferred and most particularly preferred, and in which $R^2$ and $R^3$ have the meanings given above as respectively preferred, more preferred and most preferred.

FIRST STEP OF THE METHOD (a) OF THE INVENTION

The first step of method (a) of the invention is usually carried out without further diluents. It is also possible, however, to use additionally a diluent (e.g. methylene chloride).

The first step of the method (a) of the invention can be carried out within a relatively large temperature range. In general temperatures of 10° C. to 50° C., preferably from 20° C. to 40° C., more preferably 20° C. to 30° C. Most preferably the reaction of the reaction components in the first step is initiated at 25° C. to 30° C. Further reaction is carried out at 40° C. to 45° C. followed by cooling to room temperature.

The reaction time is not critical and can be selected within a large range depending upon the size of the batch. Generally the reactants are brought together over a period of up to 150 min, preferably up to 120 min, more preferably up to 90 min. The time for further reaction is usually 3 hours with cooling overnight (i.e. in ca. 16 hours).

Work up is carried out by normal methods. In the first step of method (a) of the invention firstly evaporation is carried out under reduced pressure and the product of this step is isolated by distillation.

In carrying out the first step of method (a) of the invention in general between 0.5 mol and 5 mol, preferably between 0.5 mol and 3 mol, more preferably between 1 mol and 2 mol, most preferably between 1.2 mol and 1.7 mol of a trialkylphosphite of structure (III) are used for 1 mol alkyl 4-chloro-4,4-difluoroacetoacetate of structure (II).

SECOND STEP OF METHOD (a) OF THE INVENTION

The second step of the method (a) of the invention is optionally carried out in the presence of a diluent. All normal organic solvents that are inert for such reactions are suitable. Preferably used are optionally halogenated, aliphatic, alicyclic or aromatic hydrocarbons, for example petroleum ether, hexane, heptane, cyclohexane, methylcyclohexane, benzene, toluene, xylene, decalin, chlorobenzene, dichlorobenzene or dichloromethane; ethers, e.g. diethyl ether, diisopropyl ether, methyl-tert-butyl ether, methyl-tert-amyl ether, dioxan, tetrahydrofuran, 1,2-dimethoxyethane, 1,2-diethoxyethane or anisole; nitrites, e.g. acetonitrile, propionitrile, n- or iso-butyronitrile or benzonitrile; amides, e.g. N,N-dimethylformamide, N,N-dimethylacetamide, N-methylformanilide, N-methylpyrrolidone or hexamethylphosphoramide; sulphoxides, e.g. dimethyl sulphoxide; or sulphones, e.g. sulpholane.

The second step of method (a) of the invention can be carried out within a larger temperature range. In general temperatures of 10° C. to 100° C. are used, preferably the reaction components are mixed at temperatures of 20° C. to 30° C. and then reacted at temperatures of 30° C. to 100° C., preferably at 50° C. to 75° C.

The reaction time is not critical and can be selected over a wide range dependent upon the size of the batch. In general the reactants are mixed within a period of a few minutes to 60 min, preferably within 10 to 30 min, and then allowed to react for several hours, preferably for up to 24 hours, more preferably for up to 20 hours.

Work up is carried out by normal methods. In the second step the reaction mixture is cooled to room temperature, washed with sodium chloride solution and water, the crude product is dried and evaporated under reduced pressure. The enamine of structure (VI) is then freed of further impurities by distillation.

In carrying out the second step of the method (a) of the invention generally between 2.5 mol and 5 mol, preferably between 3 mol and 5 mol, more preferably between 2 mol and 4 mol of the amine of structure (V) are used for 1 mol alkyl phosphonate of structure (IV).

THIRD STEP OF METHOD (a) OF THE INVENTION

The hydrolysis in the third step of method (a) of the invention is carried out in the presence of an acid, preferably sulphuric acid, phosphoric acid or hydrochloric acid, which is optionally diluted with water, more preferably hydrochloric acid, most preferably mixtures of hydrochloric acid and water.

The third step of method (a) of the invention can be carried out over a wider temperature range. In general temperatures of 10° C. to 50° C., preferably 20° C. to 30° C. are used.

The reaction time is not critical and a wide range can be selected depending on the size of the batch. In general the reactants are mixed over a period of a few minutes up to 60 min, preferably between 10 min to 30 min and allowed to react for several hours preferably for up to 24 hours, more preferably up to 20 hours.

Work up is carried out by normal methods. In the third step the reaction mixture is usually extracted with a suitable solvent, washed with sodium chloride solution and sodium hydrogen carbonate solution, the crude product is dried and evaporated under reduced pressure. The alkyl 4,4-difluoroacetoacetates of structure (I) are then freed of further impurities by distillation.

In carrying out the third step of method (a) of the invention in general 0.5 mol and 5 mol, preferably between 1 mol and 5 mol, more preferably between 1 mol and 2.5 mol of acid are used for 1 mol enamine of structure (VI).

METHOD (b) OF THE INVENTION

In method (b) of the invention alkyl chlorodifluoroacetates of structure (VII) and alkyl acetates of structure (VIII) are used in which R stands preferably for $C_1$-$C_8$-alkyl, more preferably for $C_1$-$C_6$-alkyl, most preferably for methyl, ethyl, n-, isopropyl, n-, iso-, sec-, tert-butyl, and most especially for methyl or ethyl.

Method (b) of the invention is carried out in the presence of a suitable base. All normal inorganic and organic bases are suitable. These include preferably alkaline earth and alkali metal hydrides, amides, alcoholates, for example sodium hydride, sodium amide, lithium diisopropylamide (LDA), sodium methylate, sodium ethylate, potassium tert.-butylate, more preferred is lithium diisopropylamide (LDA) and sodium hydride.

Method (b) of the invention is carried out in the presence of a diluent. All normal organic solvents that are inert for such reactions are suitable. Preferably used are optionally halogenated, aliphatic, alicyclic or aromatic hydrocarbons, for example petroleum ether, hexane, heptane, cyclohexane, methylcyclohexane, benzene, toluene, xylene, decalin, chlorobenzene, dichlorobenzene or dichloromethane; ethers, e.g. diethyl ether, diisopropyl ether, methyl-tert-butyl ether, methyl-tert-amyl ether, dioxan, tetrahydrofuran, 1,2-dimethoxyethane, 1,2-diethoxyethane or anisole; nitrites, e.g. acetonitrile, propionitrile, n- or iso-butyronitrile or benzonitrile; amides, e.g. N,N-dimethylformamide, N,N-dimethylacetamide, N-methylformanilide, N-methylpyrrolidone or hexamethylphosphoramide; sulphoxides, e.g. dimethyl sulphoxide; or sulphones, e.g sulpholane.

Method (b) of the invention can be carried out over a wide temperature range. In general temperatures of −80° C. to +100° C., preferably −70° C. to 0° C. are used.

The reaction time is not critical and a wide range can be selected depending on the size of the batch. In general the reactants are mixed over a period of a few minutes up to 180 min, preferably between 10 min to 90 min and allowed to react for several hours preferably for up to 24 hours, more preferably for up to 16 hours.

Work up is carried out by normal methods. Usually the reaction mixture is neutralised, the phases are separated, washed with sodium chloride solution, the crude product is dried and evaporated under reduced pressure. The alkyl 4-chloro-difluoroacetoacetates of structure (II) are then freed of further impurities by distillation.

In carrying out method (b) of the invention in general between 0.5 mol and 5 mol, preferably between 1 mol and 5 mol, more preferably between 1 mol and 2.5 mol alkyl acetate of structure (VIII) are used for 1 mol alkyl chlorodifluoroacetate of structure (VII).

All steps of the methods (a) and (b) of the invention are normally carried out at normal pressures. It is possible, however, to carry out individual or all steps under high or reduced pressure—generally between 0.1 and 50 bar, preferably between 1 bar and 10 bar.

The alkyl 4,4-difluoroacetoacetates obtainable by method (a) of the invention are valuable intermediates for the preparation of difluoromethyl-substituted pyrazolylcarboxylic acid and thiazolylcarboxylic acid derivatives that are in turn precursors for compounds with antifungal activity (cf. e.g. WO 02/08197 and DE-A 102 15 292).

For example, alkyl 4,4-difluoroacetoacetates can be first converted into alkyl 2-(difluoracetyl)-3-alkoxy acrylates in high yields (over 90% with the ethyl ester, cf. preparation examples) with acetic anhydride and trialkyl orthoformates. Cyclisation with methyl hydrazine gives 1-methyl-3-difluoromethyl-pyrazole4-carboxylic acid (in the case of the ethyl ester in a yield of over 65%). The wrong isomer (1-methyl-5-difluoromethyl-pyrazole4-carboxylic acid) can be separated by crystallisation. The conversion can be illustrated by the following reaction scheme:

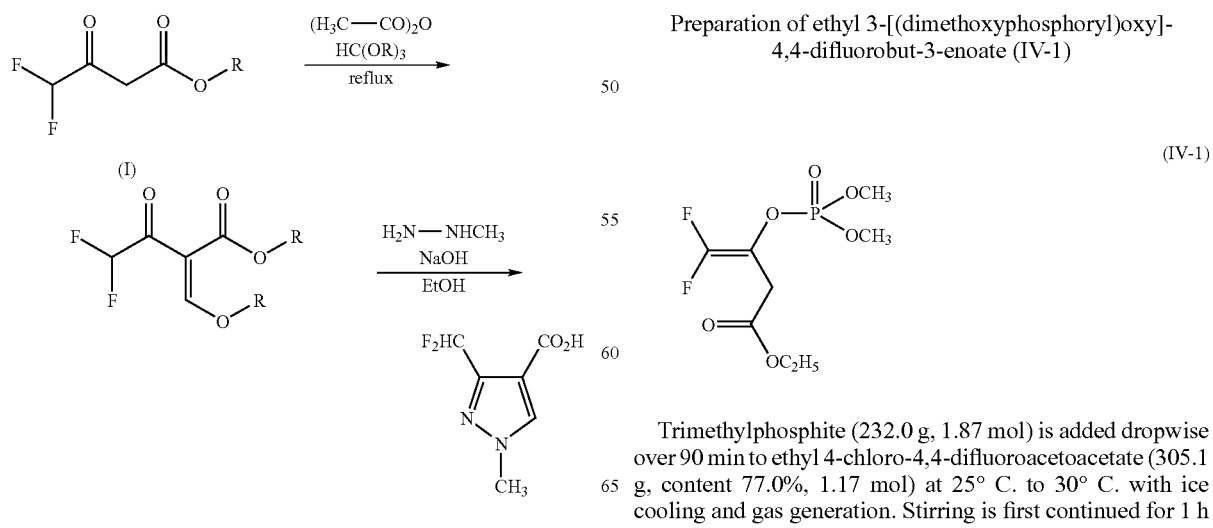

Also the alkyl 4,4-difluoroacetoacetates can be first chlorinated when the mono- and dichlorinated products (alkyl 2,2-dichloro-4,4-difluoro-3-oxobutanoate and alkyl 2-chloro-4,4-difluoro-3-oxobutanoate) are obtained, both of which can be reacted almost quantitatively with thioacetamide to form alkyl 3-methyl4-difluoromethylthiazole-5-carboxylates (cf. following scheme):

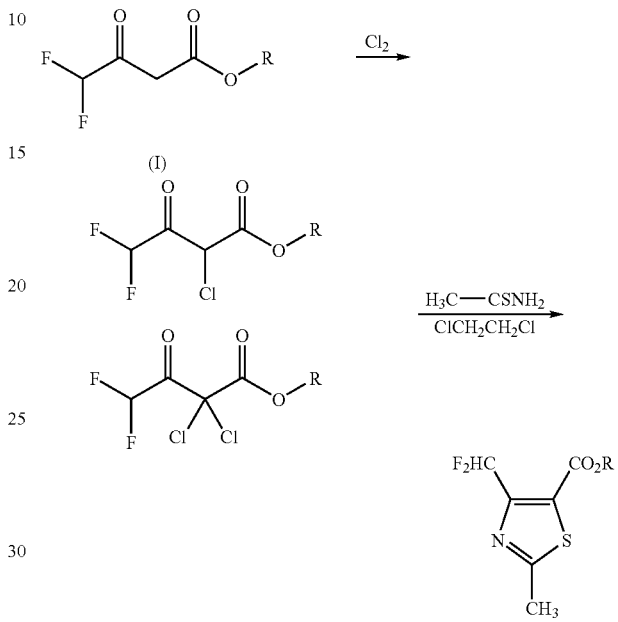

The preparation according to the invention of alkyl 4,4-difluoroacetoacetates as well as their use for the preparation of difluoromethyl-substituted heterocycles is discussed in the following examples that illustrate further the above description. However, the examples are not to be interpreted in a limiting manner.

PREPARATION EXAMPLES

Example 1

Step 1:

Preparation of ethyl 3-[(dimethoxyphosphoryl)oxy]-4,4-difluorobut-3-enoate (IV-1)

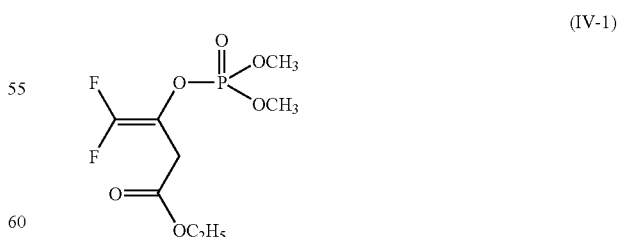

Trimethylphosphite (232.0 g, 1.87 mol) is added dropwise over 90 min to ethyl 4-chloro-4,4-difluoroacetoacetate (305.1 g, content 77.0%, 1.17 mol) at 25° C. to 30° C. with ice cooling and gas generation. Stirring is first continued for 1 h at 30° C., then for 3 h at 40° C. to 45° C. For work up the reaction mixture is cooled to room temperature (ca. 16 h) and evaporated under reduced pressure. The crude product is purified further by distillation.

302.0 g (97%, 91% of theory) ethyl 3-[(dimethoxyphosphoryl)oxy]-4,4-difluorobut-3-enoate (boiling point 92-95° C. at 0.4 hPa) are obtained.

Step 2:

Preparation of ethyl 3-(diisopropylamino)-4,4-difluorobut-3-enoate (VI-1)

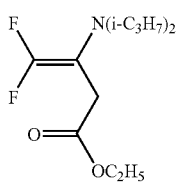

(VI-1)

Diisopropylamine (15.2 g, 0.15 mol) is added dropwise over 10 min to a solution of ethyl 3-[(dimethoxyphosphoryl)oxy]-4,4-difluorobut-3-enoate (IV-1) (14.2 g, 97%, 0.05 mol) in 100 ml methyl-tert-butyl ether. After 19 h heating under reflux the reaction mixture is cooled to room temperature, washed twice with 10 ml 10% sodium chloride solution each time, dried over sodium sulphate, filtered and evaporated under reduced pressure. The residue was distilled for further use. 8.8 g (95%, 67.4% of theory) of ethyl 3-(diisopropylamino)-4,4-difluorobut-3-enoate are obtained (boiling point 55-57° C. at 0.5 hPa).

Steps 2 and 3:

Preparation of ethyl 4,4-difluoroacetoacetate (I) without isolation of ethyl 3-(diisopropylamino)-4,4-difluorobut-3-enoate (VI-1)

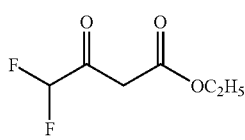

(I)

Diisopropylamine (2811.6 g, 27.8 mol) is added dropwise over 10 min to a solution of ethyl 3-[(dimethoxyphosphoryl)oxy]-4,4-difluorobut-3-enoate (IV-1) (2570 g, 98.8%, 9.26 mol) in methyl-tert-butyl ether (18.5 l) at 20° C. Stirring is continued for 20 h under reflux (57° C). At 20° C. to 25° C. with cooling a solution of 2037 g concentrated hydrochloric acid in 4080 ml water is then added dropwise and stirring is continued for 20 h. Two phases are formed which are then separated. The aqueous phase is extracted twice with 2.3 l methyl-tert-butyl ether each time. The combined organic phases are washed with 2.8 l 10% sodium chloride solution, 10% sodium hydrogen carbonate solution and again with 10% sodium chloride solution, dried over sodium sulphate, filtered and evaporated under reduced pressure. The crude product is purified by distillation.

1179 g (92%, 76.6% of theory) ethyl 4,4-difluoroacetoacetate is obtained.

Example 2

Preparation of ethyl 4-chloro-4,4-difluoracetoacetate (II)

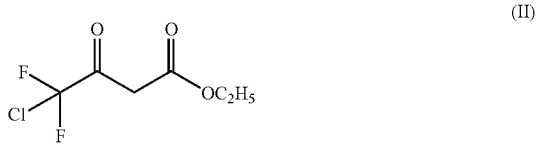

312.6 g (3.09 mol) diisopropylamine are dissolved in 1.55 l tetrahydrofuran and cooled to −70° C. 852.9 g (3.08 mol) n-butyllithium (2.5 molar in n-hexane) are added dropwise to this solution at −60° C. over 80 min and stirring is continued for 45 min at −70° C. The temperature is raised briefly to −20° C. and immediately cooled again to −70° C. Next at −60° C., 264.3 g (3.0 mol) ethyl acetate are added dropwise over 50 min. At the same temperature 242.7 g ethyl chlorodifluoroacetate are added dropwise over 30 min, stirring is continued for 3 h at −65° C. to −70° C. and then the temperature is allowed to rise to room temperature. On reaching −5° C. 1500 ml 4 N HCl are added and the reaction mixture is allowed to stand for 16 h. The aqueous phase (pH 6-7) is separated, the organic phase is washed with 750 ml 2 N HCl and 1200 ml saturated sodium chloride solution. The organic phases are dried over sodium sulphate, filtered and evaporated under reduced pressure. The crude product is distilled for further purification.

282.9 g (92%, 86.3% of theory) of ethyl 4-chloro-4,4-difluoroacetoacetate is obtained.

Example 3

Preparation of ethyl chlorodifluoroacetate (VII)

504.3 g (3.87 mol) chlorodifluoroacetic acid and 5.0 g p-toluenesulphonic acid are dissolved in 775 ml methylene chloride and treated at room temperature with 311.6 g (6.76 mol) ethanol over 30 min (temperature rise to 33° C.). Stirring is continued under reflux for 38 h with a water trap and then cooled to room temperature. For work up washing is carried out with water (200 ml), saturated sodium hydrogen carbonate solution (200 ml) and again with water (200 ml), dried over sodium sulphate, filtered and the solvent is distilled off. Finally further purification is carried out by fractional distillation.

488.9 g (98%, 78.5% of theory) of ethyl chlorodifluoroacetate (boiling point 94-96° C.) are obtained.

Example 4

Preparation of 1-methyl-5-difluoromethy-pyrazole-4-carboxylic acid

A solution of 527.8 g (11.45 mol) methylhydrazine in 0.7 l ethanol is added dropwise over 3.5 h to a solution of 2394 g (10.35 mol) ethyl 2-(difluoroacetyl)-3-ethoxyacrylate in 5.4 l ethanol at −15° C. to −5° C. and stirring is continued for 16 hours. Then 560 g (14 mol) sodium hydroxide and 3.5 l water are added and stirred is continued for 7 h at 50° C. The reaction mixture is cooled and evaporated under reduced pressure. The residue is taken up in 6 l water and 7 kg ice and washed with dichloromethane (once 3 l, once 2 l). The ice-cold aqueous phase is adjusted to pH 2 with concentrated hydrochloric acid, the precipitate product is filtered off and dried in a drying cabinet. The crude product is dissolved in 8 l isopropanol (hot) under reflux, cooled, stirred for 30 min at 0° C. to 5° C., filtered, washed with 1.4 l isopropanol (5° C.) and dried in a drying cabinet at 40° C.

1226.4 g (99.8%, 67.1% of theory) of 1-methyl-5-difluoromethylpyrazole-4-carboxylic acid [Log P (pH 2.3)=0.52] are obtained.

Example 5

Preparation of ethyl 3-methyl-4-difluoromethylthiazole-5-carboxylic acid 28 g (0.27 mol) thioacetamide are added to a mixture of ethyl 2-chloro-4,4-difluoro-3-oxobutanoate (50.4%) and ethyl 2,2-dichloro4,4-difluoro-3-oxobutanoate (68.2 g, 0.2 mol, 50.4% monochloro compound, 19.2% dichloro compound) in 500 ml 1,2-dichlorethane, heated for 2 h under reflux and then stood for 16 h. 300 ml saturated sodium hydrogen carbonate solution is then added slowly with stirring and the phases are separated. The organic solution is dried with sodium sulphate and evaporated under reduced pressure. The residual solution is filtered, washed with 20 ml methylene chloride and evaporated under reduced pressure.

53.4 g (72%, 86.7% of theory) of ethyl 3-methyl-4-difluoromethyl-thiazole-5-carboxylate [Log P (pH 2.3)=2.18] are obtained.

The determination of the log P values reported in the above tables and preparation examples is carried out in compliance with EEC Directive 79/831 Annex V.A8 by HPLC (High Performance Liquid Chromatography) on a reverse phase column (C 18). Temperature: 43° C.

The determination is carried out in the acid region at pH 2.3 with 0.1% aqueous phosphoric acid and acetonitrile as eluents; linear gradient of 10% acetonitrile to 90% acetonitrile.

Calibration is carried out with unbranched alkan-2-ones (with 3 to 16 carbon atoms) the log P values of which are known (determination of the log P values on the basis of retention times by linear interpolation between two sequential alkanones).

The invention claimed is:
1. A method of preparing alkyl esters of 4,4-difluoroacetoacetic acid of formula (I)

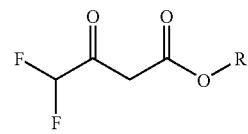

in which R represents alkyl,
comprising
(a) in a first step, reacting an alkyl ester 4-chloro-4,4-difluoroacetoacetic acid of formula (II)

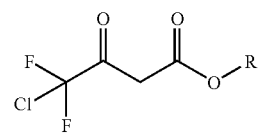

in which R represents alkyl,
with a trialkylphosphite of formula (III)

in which each $R^1$ independently of the others represents $C_1$-$C_4$-alkyl, to give a alkylphosphonate of formula (IV)

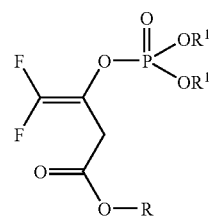

in which R and $R^1$ have the meanings described above,
(b) in a second step, reacting the alkylphosphonate of formula (IV) with an amine of formula (V)

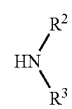

in which
$R^2$ and $R^3$ independently of each other represent hydrogen or $C_1$-$C_8$-alkyl, or $R^2$ and $R^3$ together represent —$CH_2$—$CH_2$—O—$CH_2$—$CH_2$—, —$CH_2$—$CH_2$—S—$CH_2$—$CH_2$—, or —$CH_2$—$CH_2$—N($R^4$)—$CH_2$—$CH_2$—, and
$R^4$ stands for hydrogen or $C_1$-$C_8$-alkyl,
optionally in the presence of a diluent,
to give an enamine of formula (VI)

(VI)

[structure of formula VI: enamine with F, F, NR²R³, and CH₂C(=O)O—R]

in which R, $R^2$, and $R^3$ have the meanings described above, and (c) in a third step, condensing the enamine of formula (VI) in the presence of an acid.

2. A method according to claim 1, in which the alkyl 4-chloro-4,4-difluoroacetoacetate of formula (II) used in the first step is prepared by reacting an alkyl chlorodifluoroacetate of formula (VII)

(VII)

[structure: ClCF₂C(=O)O—R]

in which R represents alkyl, with an alkyl acetate of formula (VIII)

(VIII)

[structure: H₃C-C(=O)-O-R]

in which R represents alkyl, in the presence of a base and in the presence of a diluent.

3. A method according to claim 1, in which, for compounds of formula (II), R represents $C_1$-$C_8$-alkyl.

4. A method according to claim 1, in which, for compounds of formula (II), R represents $C_1$-$C_6$-alkyl.

5. A method according to claim 1, in which
for compounds of formula (II), R represents methyl, ethyl, n- or iso-propyl, or n-, iso-, sec-, or tert-butyl,
for compounds of formula (III), each $R^1$ independently of the others represents methyl, ethyl, n- or iso-propyl, or n-, iso-, sec-, or tert-butyl, and for compounds of formula (V), $R^2$ and $R^3$ independently of each other represent hydrogen, methyl, ethyl, n- or iso-propyl, or n-, iso-, sec-, or tert-butyl, or $R^2$ and $R^3$ together represent —CH₂—CH₂—O—CH₂—CH₂—.

6. A method according to claim 1, in which the first step is carried out without diluent.

7. A method according to claim 1, in which the hydrolysis in the third step is carried out in the presence of sulphuric acid, phosphoric acid, or hydrochloric acid, each of which is acids optionally diluted with water.

8. An alkyl phosphonate of formula (IV)

(IV)

[structure: F₂C=C(OP(=O)(OR¹)(OR¹))CH₂C(=O)O—R]

in which
R represents alkyl, and
each $R^1$ independently represents $C_1$-$C_4$-alkyl.

9. An enamine of formula (VI)

(VI)

[structure: F₂C=C(NR²R³)CH₂C(=O)O—R]

in which
R represents alkyl,
$R^2$ and $R^3$ independently of each other represent hydrogen or $C_1$-$C_8$-alkyl, or $R^2$ and $R^3$ together represent —CH₂—CH₂—O—CH₂—CH₂—, —CH₂—CH₂—S—CH₂—CH₂—, or —CH₂—CH₂—N(R⁴)—CH₂—CH₂—, and
$R^4$ stands for hydrogen or $C_1$-$C_8$-alkyl.

* * * * *